United States Patent [19]

Clark et al.

[11] Patent Number: 5,057,119
[45] Date of Patent: Oct. 15, 1991

[54] APPARATUS AND METHODS FOR ATTACHING AND DETACHING AN ULTRASONIC ACTUATED BLADE/COUPLER AND AN ACOUSTICAL MOUNT THEREFOR

[75] Inventors: Richard J. Clark, Norfolk, Mass.; Alan E. Thomas, Ocean City, N.J.

[73] Assignee: Ultracision Inc., Smithfield, R.I.

[21] Appl. No.: 642,879

[22] Filed: Jan. 18, 1991

Related U.S. Application Data

[63] Continuation-in-part of Ser. No. 448,862, Dec. 12, 1989.

[51] Int. Cl.⁵ .................. A61B 19/02; A61B 17/00; F16D 7/02; B25B 23/159
[52] U.S. Cl. .................. 606/169; 606/167; 464/37; 81/477; 192/56 R
[58] Field of Search .................. 606/167, 169, 172; 81/473, 477; 192/56 R; 464/30, 37

[56] References Cited

U.S. PATENT DOCUMENTS

| 2,441,038 | 5/1948 | Siesel | 64/29 |
|---|---|---|---|
| 2,797,564 | 7/1957 | Bonneau et al. | 64/29 |
| 2,831,648 | 4/1958 | Meeger et al. | 464/37 |
| 3,228,209 | 1/1966 | Hersey | 192/56 R |
| 3,229,793 | 1/1966 | Jacobson | 192/56 R |
| 3,373,491 | 3/1968 | Montelius | 30/339 |
| 3,441,115 | 4/1969 | Gunther | 192/56 R |
| 3,597,582 | 8/1971 | Goode et al. | 128/218 |
| 3,799,168 | 3/1974 | Peters | 128/303 |
| 3,804,096 | 4/1974 | Gonser | 128/303 |
| 3,964,163 | 6/1976 | Russo | 30/166 |
| 4,006,608 | 2/1977 | Vuceta | 192/56 R |
| 4,014,343 | 3/1977 | Esty | 128/303 |
| 4,123,840 | 11/1978 | Rumer, Jr. | 29/453 |
| 4,180,162 | 12/1979 | Magney | 206/359 |
| 4,359,052 | 11/1982 | Staub | 128/303 |
| 4,674,498 | 6/1987 | Stasz | 128/303 |
| 4,679,468 | 7/1987 | Gray | 81/121 |
| 4,730,376 | 3/1988 | Yamada | 29/239 |
| 4,735,202 | 4/1988 | Williams | 128/305 |
| 4,754,754 | 7/1988 | Garito et al. | 128/303 |
| 4,826,490 | 5/1989 | Byrne et al. | 604/198 |
| 4,832,021 | 5/1989 | Kuhl et al. | 128/303 |
| 4,846,025 | 7/1989 | Keller et al. | 81/3.09 |

Primary Examiner—Richard J. Apley
Assistant Examiner—Karen G. Horowitz
Attorney, Agent, or Firm—Nixon & Vanderhye

[57] ABSTRACT

A delivery system for attaching and detaching an ultrasonic surgical blade/coupler and an acoustical mount. An adaptor sleeve receives and encapsulates the blade to avoid accidents resulting from the sharp edge of the blade. In a two-piece embodiment hereof, a cylindrical member receives the sleeve and a ratcheting mechanism is provided between the adaptor and member to facilitate rotation of the adaptor and coupler upon rotation of the member up to a predetermined torque, ensuring threaded connection between the coupler and acoustical mount sufficient for transmission of ultrasonic energy. To remove the blade/coupler, the member is rotated in the opposite direction, whereby unlimited torque may be applied through the ratchet mechanism to unthread the coupler from the mount. In a one-piece embodiment hereof, the adaptor integrally carries an element pivotal for movement about an axis parallel to the axis of the sleeve to engage one or the other of projections on the adaptor flange to rotate the adaptor in either direction. In one direction, the element slips past the projection at a predetermined magnitude of torque.

13 Claims, 4 Drawing Sheets

APPARATUS AND METHODS FOR ATTACHING AND DETACHING AN ULTRASONIC ACTUATED BLADE/COUPLER AND AN ACOUSTICAL MOUNT THEREFOR

RELATED APPLICATIONS

This application is a continuation-in-part of application Ser. No. 07/448,862, filed Dec. 12, 1989, of like title.

BACKGROUND AND SUMMARY OF THE INVENTION

The present invention relates generally to an ultrasonic surgical device delivery system and particularly relates to apparatus and methods for facilitating attachment and detachment of an ultrasonically-actuated blade/coupler assembly and an acoustical mount therefor.

Ultrasonic surgical devices for performing a variety of surgical procedures are well known. Generally, these surgical devices are hand-held instruments connected to a source of ultrasonic energy. The ultrasonic energy is transmitted through a connection or mount between the ultrasonic energy source and a hand-held coupler which mounts the surgical tool, for example, a surgical blade mounted at the tip of the hand-held coupler. Ultrasonic energy is therefore transmitted through the coupler to the surgical blade to facilitate a precise surgical incision.

Ultrasonic surgical devices, however, are not without problems when used. For example, an acoustically-actuated surgical device should be used in a sterile field. Ready attachment and detachment of the surgical device relative to the ultrasonic energy source is highly desirable. Traditionally, a screw-type mechanism has been employed to secure the ultrasonic surgical device to its acoustical mount so that the ultrasonic energy may be transmitted through the mount to the surgical device. Because of the need for a sterile environment, the surgical device must be readily attached to the acoustical mount for use in a manner which maintains the sterile field. Quick detachment of the surgical device from its acoustical mount after use for sterilization or disposal is also highly desirable.

It will be appreciated that the connection between the surgical device and the ultrasonic energy source requires a tight union so that ultrasonic energy may be efficiently transmitted to the device at the desired power levels. When a screwthread is used, the surgical device is often over-tightened to the acoustical mount by the surgeon, nurse or technician in order to ensure that ultrasonic energy is properly transmitted to the surgical device. Typically, this causes difficulties, not only when attaching the surgical device and its mount, but also when detaching the surgical device from the mount after use, i.e., it is often overtightened and therefore difficult to detach. Also, when attaching and detaching the surgical device and the acoustical mount, there is the obvious danger of injury to the doctor, nurse or technician as a result of contact with the surgical device itself, e.g., the blade. Additionally, it is very difficult for surgeons, nurses or technicians to connect and disconnect the surgical device and its acoustical mount in a sterile field using typical fastening devices such as pliers, wrenches and the like and without causing injury.

According to the present invention, there is provided an ultrasonic surgical device delivery system that overcomes the foregoing and other problems associated with the attachment and detachment of an ultrasonic surgical device and its acoustical mount and provides apparatus and methods facilitating attachment and detachment of an ultrasonic surgical device and an acoustical mount therefor affording various advantages in construction, operation and use in comparison with traditional prior systems. Particularly, the present invention, in a preferred embodiment thereof, provides an adaptor having a generally cylindrical sleeve and a radial flange at one end, the flange having a conical surface for directing the surgical device into the sleeve. The surgical device may, for example, include a blade/coupler having a surgical blade at one end and an internally threaded female connection at its opposite end for connection to the acoustical mount. Flats are provided along both the coupler of the surgical device and the interior of the adaptor sleeve whereby, when the adaptor receives the blade/coupler, the adaptor and coupler may be rotated as a unit.

Two different embodiments for rotating the adaptor and hence adaptor/coupler combination are provided. In one embodiment, a separate cooperating cylindrical member having a radially extending end flange is received over the sleeve of the adaptor and is rotatable relative to the adaptor. In this form, the rearwardly facing annular surface of the adaptor flange is provided with a plurality of cam surfaces which form part of a circular ratchet mechanism. The cam surfaces may, for example, comprise ramps in each quadrant of the rearwardly facing annular surface and which ramps terminate in end stops. The end flange of the cylindrical member preferably has a pair of cam followers, e.g., end projections, for engaging two of the cam surfaces along the rearwardly facing annular surface of the adaptor flange, the projections being provided at diametrically opposed locations. Additionally, the cylindrical member is provided with diametrically opposed, radially extending wings preferably extending from the end flange the full length of the member, such wings facilitating manual purchase of the member and its rotation relative to the adaptor. The wings are preferably circumferentially spaced 90° from the end projections. In this manner, the portions of the end flanges of the cylindrical member carrying the projections may resiliently flex in an axial rearward direction. The cylindrical member is received about the adaptor sleeve and secured against axial movement relative thereto by spring-biased fingers at the end of the adaptor sleeve remote from the adaptor flange.

Preferably, the blade/coupler, adaptor and cylindrical member are provided in a sterile package, in assembly or not, as desired. In use, the blade/coupler, adaptor and member are removed from their sterile packaging and, if not assembled, are assembled one to the other and to the blade/coupler. Particularly, the blade end of the blade/coupler surgical device is inserted into the adaptor sleeve, the conical end surface of the adaptor facilitating that insertion by guiding the blade into the sleeve. The blade/coupler is also rotationally aligned with the adaptor sleeve such that the flats on the coupler engage the flats within the bore of the sleeve. The interior edges of the conical surface engages stops carried by the blade/coupler limiting its axial movement into the adaptor. It will be appreciated that the blade is wholly received within the adaptor sleeve. Thus, the sleeve protects an individual against exposure to the blade during attachment or detachment of the device relative to the acoustical mount.

To attach the surgical device to the mount, the blade/coupler is threaded on the mount. When the coupler is loosely tightened to the mount, the wings on the cylindrical member are grasped and the member is rotated in the conventional screw-threading direction. The end projections on the member frictionally engage the cam surfaces, and consequently, the adaptor and member are rotatable as a unit to further tighten the blade/coupler to the acoustical mount. As the joint tightens and the resistance to further threading increases, the projections start to slide along the cam surfaces while continuing to apply torque to the adaptor and the coupler whereby the coupler is further tightened. Particularly, the end projections move up the ramps, causing the flange carrying the projections to resiliently flex or yield in an axial rearward direction and hence cause greater frictional engagement between the end projections and the cam surfaces. At a predetermined torque, the projections will move past the high points or trailing ends of the cam surfaces and spring back to engage the leading portions of the next cam surfaces. Thus, upon rotating the member further, a ratcheting action is provided at a predetermined torque value between the cylindrical member and the adaptor. In this manner, the individual attaching the blade/coupler to the acoustical mount will recognize that sufficient torque has been applied to the blade/coupler to ensure its connection with the acoustical mount in such manner that the ultrasonic energy will be efficiently transferred to the surgical device and this will be accomplished without over-tightening the connection. The adaptor and member are then removed from the blade/coupler assembly and the ultrasonic surgical device is ready for use.

To detach the surgical device from the acoustical mount after use, the adaptor and member are applied to the blade end of the device similarly as previously described. The cylindrical member, however, is rotated in the opposite direction, i.e., in a direction to unthread the blade/coupler from the acoustical mount. The projections on the member will thus engage the end stops of the cam surfaces and rotate the adaptor and coupler to provide the necessary unthreading action. Essentially unlimited torque may be applied to the member when rotated in the unthreading direction. Importantly, the unthreading action is provided with the blade completely encapsulated within the sleeve of the adaptor, thus protecting the individual removing the surgical device from its mount from cuts and puncture wounds. Once removed, the entire blade/coupler, adaptor and cylindrical member assembly may be thrown away. Alternatively, the adaptor and member sub-assembly may be removed from the blade/coupler, whereby the latter may be sterilized for reuse.

In another preferred embodiment of the present invention, the blade/coupler adaptor comprises an integrated one-piece unit formed of plastic material and which serves as the complete wrench, without the addition of a separate member as in the prior two-piece embodiment, for attaching and detaching the blade/coupler to and from the mount, respectively. More particularly, the adaptor includes a generally cylindrical sleeve with a flange at one end, together with flats along the interior of the adaptor sleeve, as previously described, for receiving the blade/coupler. In this form, however, a single unitary, generally radially projecting element or flange projects from one side of the sleeve. The element is generally rectilinear and extends parallel to the axis of the sleeve and from a position just behind, but spaced from, the flange. The element has a zone of weakness adjacent its attachment to the sleeve defining a hinge having an axis parallel to but spaced from the axis of the sleeve. The element is otherwise unconnected to the sleeve and flange and therefore may flex in opposite directions about the axis of the hinge.

A pair of projections extend from the back side of the flange for engagement by the forward edge portion of the element upon flexing movement in the opposite direction. One projection has a predetermined length in the axial direction such that when a predetermined magnitude of torque is applied by the element to the projection (and hence by the adaptor to the blade/coupler), the flange deflects under the applied load, thus moving the projection forwardly and out of the way of the element. Consequently, the element at a predetermined magnitude of applied torque may pivot past this projection. The length of the projection and thickness of the material forming the flange are predetermined to provide this deflection and movement of the element past the projection at a predetermined torque in the blade/coupler mount tightening direction.

The other projection has a greater axial extent and serves as an abutment or stop for the element when rotated in the opposite direction. Thus, to remove the blade/coupler from its mount, the blade/coupler is inserted into the sleeve and the element moved about its axis against the longer projection to rotate the adaptor and, hence, blade/coupler in a direction unthreading the blade/coupler from the mount. While a pair of elements, each associated with a pair of projections, may be provided, it is preferable to provide only one such element because it might be possible to move only one of the two elements past its projection whereby the proper magnitude of torque applied to the blade/coupler would not be of the predetermined value.

Another feature of this one-piece embodiment of the present invention resides in a rearwardly projecting portion of the sleeve, which has a wall thickness thinned down or reduced to permit inward deflection by finger pressure. That is, the end of the sleeve remote from the flange may be compressed inwardly by finger pressure. This facilitates removal of the blade/coupler from the adaptor by creating an undercut to ease pulling the adaptor from the blade/coupler.

With the foregoing features in mind, it will be readily seen that there are significant advantages and benefits afforded by the system of the present invention. For example, the surgical blade during attachment and detachment from the acoustical mount is completely encapsulated within the sleeve of the adaptor, thereby preventing injury to the individual performing those tasks. Additionally, the blade/coupler, together with the attaching and detaching mechanism, may be provided as part of a sterile package for single use and disposal. Further, the ratcheting action during attachment, described above in connection with the two-piece embodiment, and the pivoting of the element past the projection, as described above with respect to the one-piece embodiment, ensure that sufficient torque has been applied to the coupler so that the requisite ultrasonic energy will be efficiently transmitted from the ultrasonic source to the surgical device. Further tightening beyond the predetermined torque is thus not necessary and the problems associated with over-tightening are completely eliminated. The ratchet and pivoting mechanism also signals the individual attaching the device to the mount that sufficient tightness has been achieved whereby over-tightening and difficult removal is prevented. Additionally, during removal, the same delivery system is used. The one-way ratchet and the larger projection of the first and second embodiments, respectively, also enable virtually unlimited torque to be applied to the coupler in the reverse unthreading direction to facilitate its removal from the acoustical mount. Further, when removed, the adaptor and member, or the unitary adaptor, may remain attached to the blade/coupler throughout disposal to provide a protective enclosure for the blade, thereby avoiding accidents resulting from the sharp edge of the blade and transmission of infectious diseases. Both the integrated one-piece adaptor and the two-piece unit are also readily and easily used and manufactured and may be provided inexpensively of plastic materials.

Accordingly, and in accordance with a preferred embodiment of the present invention, there is provided apparatus for attaching a surgical device to a mount wherein the surgical device includes a coupler carrying a surgical tool comprising an adaptor including a sleeve for receiving the surgical tool and a flange adjacent one end of the sleeve, first means carried by the adaptor and engageable with the coupler when the surgical tool is received by the adaptor for rotating the coupler upon rotation of the adaptor and second means carried by the adaptor for rotating the adaptor to rotate the coupler. Also provided are means cooperable between the second means and the adaptor flange and responsive to movement of the second means in one direction for limiting the torque applied by the adaptor to the coupler to a predetermined magnitude thereof when the surgical tool is being attached to the mount. Third means are cooperable between the second means and the adaptor, and responsive to movement of the second means in the opposite direction, for applying a torque to the adaptor and coupler in the opposite direction in excess of the predetermined torque.

In a further preferred embodiment according to the present invention, there is provided apparatus for attaching a surgical device to a mount wherein the surgical device includes a coupler carrying a surgical tool comprising an adaptor including an elongated sleeve, having an axis, for receiving the surgical tool, a flange having an abutment, and guide surfaces carried by the adaptor and engageable with the coupler when the surgical tool is received by the adaptor for rotating the coupler upon the rotation of the adaptor. A generally radially extending element is carried by the adaptor for rotating the adaptor to rotate the coupler, the element being movable in opposite directions about an axis noncoincident with the axis of the sleeve and cooperable with the abutment in response to rotation of the element about its axis in one direction to rotate the adaptor and coupler about the axis of the sleeve and to limit the torque applied by the adaptor to the coupler to a predetermined magnitude thereof. A second abutment is carried by the flange, the element being cooperable with the second abutment in response to rotation of the element about its axis in the opposite direction for applying a torque to the adaptor and coupler in excess of the predetermined magnitude of torque.

In a further preferred embodiment according to the present invention, there is provided a method for attaching a surgical device to a mount wherein the surgical device includes a coupler carrying the surgical tool, comprising the steps of providing an adaptor having a sleeve containing the surgical tool and engageable with the coupler such that the coupler and adaptor may be rotated in one direction upon rotation of the adaptor in one direction, providing a member carried by the adaptor and movable in opposite directions, moving the member in one direction to rotate the adaptor and coupler in one rotary direction, limiting the torque applied by the adaptor to the coupler to a predetermined magnitude thereof in response to movement of the member in one direction, moving the member in the opposite direction to rotate the adaptor and coupler in the opposite rotary direction and applying a torque to the member when moving it in the opposite direction to rotate the adaptor and coupler in the opposite rotary direction, in excess of the predetermined magnitude of torque, thereby to detach the surgical device and the mount.

Accordingly, it is a primary object of the present invention to provide novel and improved apparatus and methods for attaching and detaching a surgical device relative to its energy source.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to the present preferred embodiments of the invention, examples of which are illustrated in the accompanying drawings.

Figure 1:
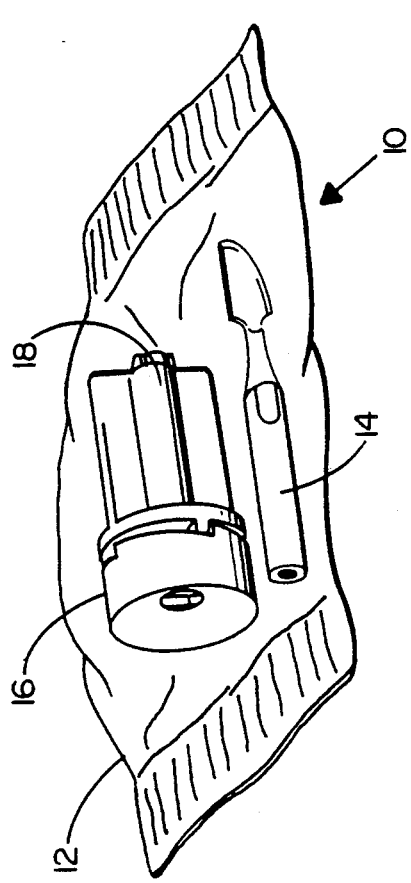
FIG. 1 is a perspective illustration of an ultrasonic surgical device delivery system constructed according to the present invention and illustrated within a sterile package.

Referring now to the drawings, there is illustrated in FIG. 1 an ultrasonic surgical device delivery system constructed according to a first embodiment of the present invention and generally designated 10. The system is illustrated encapsulated within a sterile, preferably plastic, package 12. The general parts of the delivery system 10 of this embodiment include a surgical device, e.g., a blade/coupler 14, an adaptor 16 and a cylindrical member 18. The adaptor 16 and cylindrical member 18 are shown in assembly within the package 12, while the blade/coupler 14 is illustrated as a separate part. It will be appreciated that the system may include within the sterile package 12 a complete assembly of its component parts, that is, the blade/coupler 14 may be disposed within the adaptor 16 with the member 18 assembled thereon, as will be apparent to those skilled in this art. Alternately, the component parts may be provided separately within the packaging 12 and assembled at the time of use.

Figure 2:
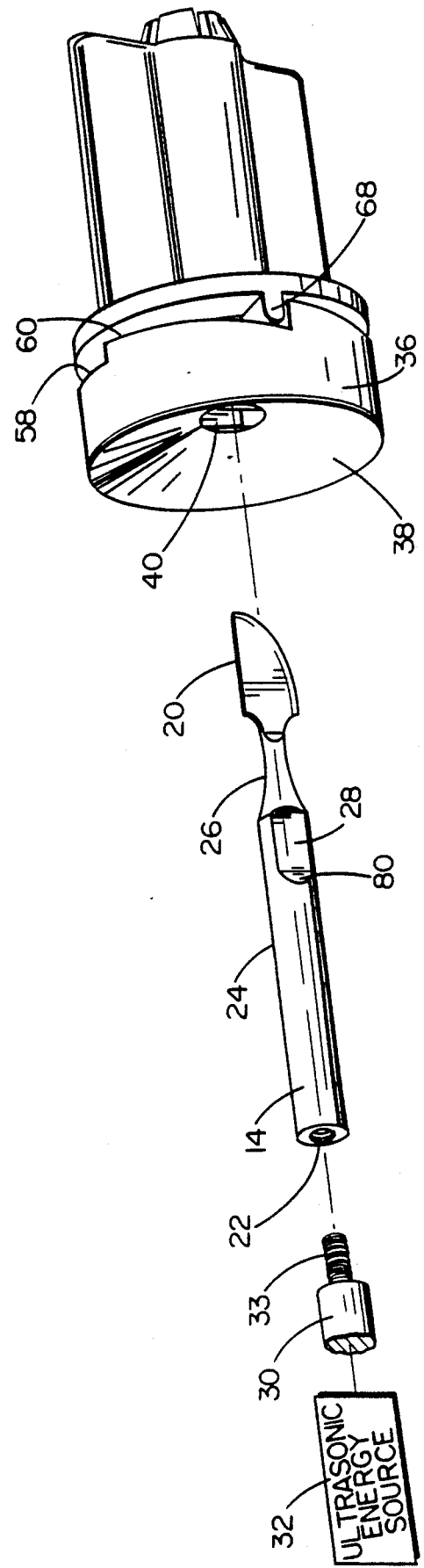
FIG. 2 is a schematic fragmentary perspective view illustrating the cooperation of the various parts of the delivery system hereof in use.

Referring now to FIG. 2, the blade/coupler 14 mounts a surgical tool 20, for example, a blade, at one end and has an internally threaded female bore 22 at its opposite end. The body 24 of blade/coupler 14 comprises a generally cylindrical member having a tapered head portion 26 terminating in blade 20. Diametrically opposed flats 28 are provided along the opposite sides of the body member 24 for reasons which will become clear. Blade/coupler 14 is adapted for threaded engagement with an acoustical mount 30 which is coupled to an ultrasonic energy source 32, whereby ultrasonic energy may be provided blade 20 for precision cutting. To effect the transmission of the ultrasonic energy, the blade/coupler 14 is screw-threaded to mount 30, the latter having an externally threaded male projection 33 for reception in the internally threaded female bore 22.

Figure 3:
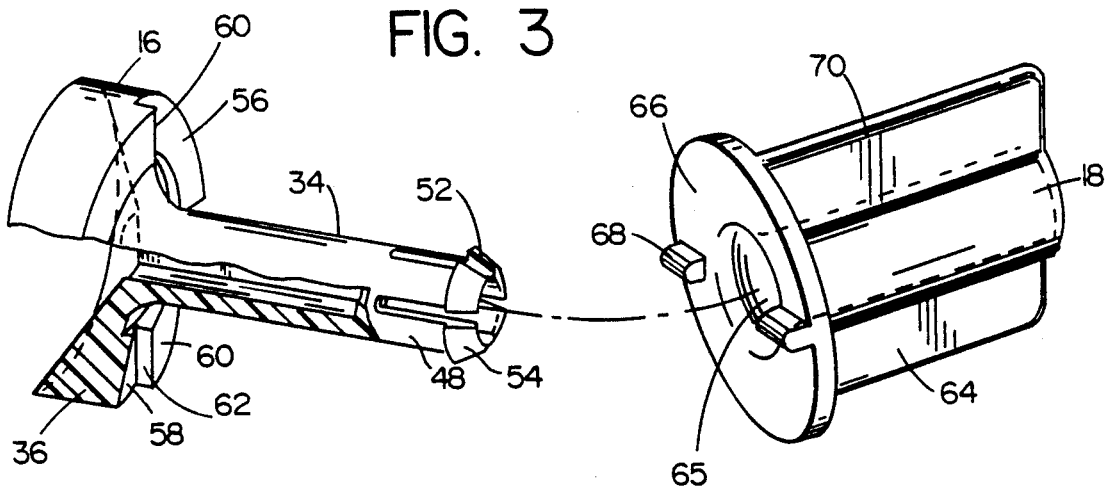
FIG. 3 is a fragmentary perspective view with parts broken out and in cross-section illustrating the cooperation between the adaptor and the cylindrical member.
Figure 4:
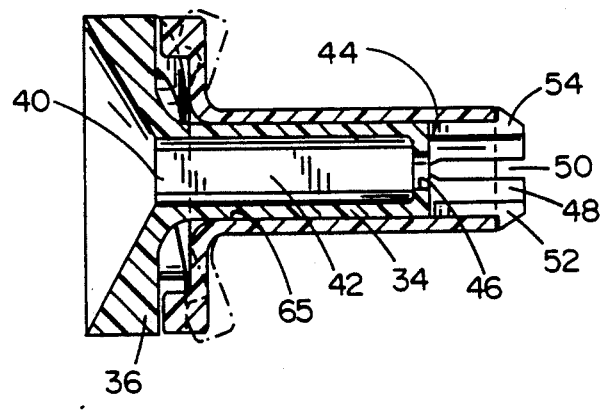
FIG. 4 is a cross-sectional view through the assemblage of the adaptor and cylindrical member illustrating the cooperation of the end projections on the cam surfaces of the member and adaptor, respectively.
Figure 5:
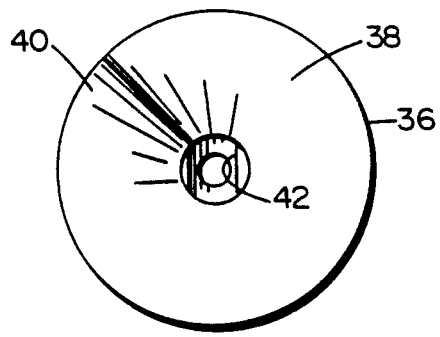
FIG. 5 is an end elevational view of the adaptor.
Figure 6:
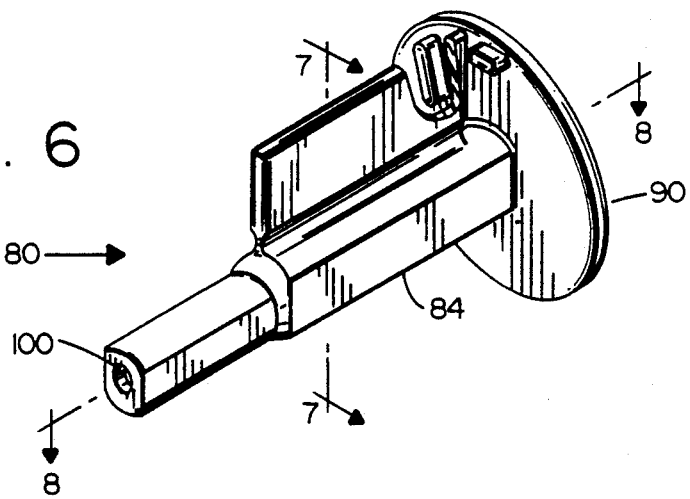
FIG. 6 is a perspective view of a one-piece adaptor or wrench according to a second embodiment of the present invention and with a part thereof broken out and in cross-section.

Turning now to FIGS. 3–5, adaptor 16 may comprise a generally cylindrical sleeve 34 terminating at one end in an enlarged radially extending flange 36. As illustrated in FIG. 2, the end face of flange 36 comprises a frustoconical surface 38 for guiding blade 20 into the bore 40 within sleeve 34. Bore 40 is provided with a pair of diametrically opposed flats 42 for registration and alignment with flats 28 on the opposite sides of blade/coupler 14 upon full insertion of blade/coupler 14 into adaptor sleeve 34, in a manner described in detail hereinafter.

The end of sleeve 34 opposite flange 36 includes an inwardly directed radial flange or end surface 44 having a reduced diameter bore opening 46 and a plurality of circumferentially spaced, axially extending, resiliently flexible fingers 48, spaced one from the other by axially extending slots 50. Each finger 48 terminates at its distal end in a radially outwardly projecting locking tip 52 having a tapered camming surface 54.

As best illustrated in FIGS. 2 and 3, the rear face of flange 36 is provided with a plurality of cam surfaces 56 at circumferentially spaced positions thereabout forming part of a ratchet mechanism. For example, cam surfaces 56 may comprise ramps, four being illustrated, and which ramps extend from low points 58 to high points 60. Each high point terminates in an axially extending end face or stop 62 at the beginning of the low point 58 of the circumferentially adjacent ramp 56.

Referring to FIGS. 2–4, cylindrical member 18 comprises a sleeve 64 having an internal bore 65 for snugly receiving sleeve 34 of adaptor 16. At one end of cylindrical member 18, there is provided a radially outwardly extending flange 66 having a pair of cam followers, e.g., a pair of diametrically opposed axially extending projections 68. Extending rearwardly from flange 66 and projecting radially outwardly from sleeve 64 are a pair of diametrically opposed wings 70 which extend the full length of member 18. From a review of FIG. 3, it will be appreciated that wings 70 are circumferentially spaced from the circumferential locations of projections 68. For example, wings 70 are spaced 90° from each of projections 68. This enables a resilient flexing (FIG. 4) of the flange 66 at each of the points of engagement of projections 68 with cam surfaces 56, in a manner to be described. Wings 70 are used to facilitate manual purchase of the cylindrical member and rotation thereof relative to adaptor 16.

In use, the delivery system is removed from the sterile package 12 in a sterile field and the blade/coupler 14 is loosely screw-threaded to the acoustical mount 30. If the blade/coupler 14 is provided in the sterile package in assembly with the adaptor 16 and member 18, then the entire assembly is loosely screw-threaded to mount 30. If not, blade/coupler 14 may be separately loosely screw-threaded to mount 30. Adaptor 16 and member 18 may be assembled one with the other (if not previously provided in assembly in sterile package 12) by inserting sleeve 34 into bore 65 of sleeve 64 of member 18. It will be appreciated that, upon receiving sleeve 34, member 18 cams the locking tips 52 radially inwardly until the opposite end of member 18 clears the locking tips, at which time the fingers 48 resilient spring back to the position illustrated in FIG. 4, locking member 18 on adaptor 16. The relative dimensions of adaptor 16 and member 18 are such that the locking action occurs only when projections 68 bear against the lower ends, i.e., leading edges 58 of the ramps 56, whereby member 18 is prevented from axial movement along adaptor 16. Blade/coupler 14 is then inserted into the sub-assembly of adaptor 16 and member 18 by inserting blade 20 into bore 40 of sleeve 34 such that flats 28 are aligned with flats 42 within the bore. The end edges of the bore adjacent the conical surface 38 engage the rearwardly extending radial enlargements 80 (FIG. 2) at the rear end of flats 28 to limit the extent to which the blade/coupler 14 is inserted into sleeve 34.

It will be appreciated that, with flats 28 and 42 aligned and bearing against one another, the entire sub-assembly of adaptor 16 and member 18 may be rotated as a unit. Thus, to tighten the threaded connection between the blade/coupler 14 and mount 30, wings 70 on the member 18 are grasped and rotated, causing the adaptor 16 and the blade/coupler 14 to rotate as a unit, hence tightening the threaded connection. The force transmission between member 18 and adaptor 16 is provided by the frictional engagement between projections 68 and ramps 56. As increased torque is applied and resistance to tightening increases, the projections 68 overcome their frictional resistance on ramps 56 and begin to slide along ramps 56. At a predetermined torque value, the projections 68 reach the ends or high point 60 of ramps 56 and slip past those end points onto the low points or leading edges of the circumferentially adjacent ramps. Upon continued rotation of member 18 about adaptor 16, a circumferential ratcheting action occurs, at which time the individual applying the torque recognizes that sufficient torque has been applied to ensure a sufficiently tight threaded connection between blade/coupler 14 and mount 30 whereby the ultrasonic energy may be efficiently transmitted to blade 20. The adaptor 16 and member 18 are then simply withdrawn from the blade/coupler 14, exposing the blade 20 for use. It will be appreciated that when the blade/coupler 14 is applied to mount 30, blade 20 resides wholly within sleeve 34 of adaptor 16. Consequently, the individual applying blade/coupler 14 to mount 30 is protected from accidents resulting from the sharp edge of the blade. Additionally, by utilizing the ratcheting action, the predetermined torque necessary to screw-thread blade/coupler 14 to the transmission element 30 is not be exceeded. This prevents over-tightening and consequent difficulties in removing blade/coupler 14 from mount 30.

To remove blade/coupler 14 from mount 30, the individual grasps wings 70 of member 18 and rotates member 18 in the opposite or unthreading direction. It will be appreciated that the projections 68, upon rotation in the opposite direction, will engage against end stops 62. At this time, virtually unlimited torque may be applied to member 18 and which torque is transmitted through the cooperating projections 68, end stops 62 and flats 28 and 42 to unthread blade/coupler 14 from mount 30. Again, blade 20 is wholly encapsulated within the sleeve 34 during this unthreading action, thereby protecting the individual from sharps accidents. Upon removing blade/coupler 14 from mount 30, the entire assembly, including blade/coupler 14, adaptor 16 and member 18, may then be thrown away. Alternatively, if blade/coupler 14 is non-disposable, it can be removed from the sub-assembly of adaptor 16 and member 18 for subsequent sterilization and re-use.

Preferably, adaptor 16 is formed of a polycarbonate, for example, Lexan, while the member 18 may be formed of a polypropylene. By using such materials, it will be appreciated that flange 66 of member 18 is to a degree resilient. Thus, when member 18 is rotated relative to adaptor 16, with projections 68 riding upwardly on ramps 56, the flange will flex rearwardly, as indicated by the dashed lines in FIG. 4.

In a second preferred embodiment of the present invention, there is provided an adaptor, generally designated 81, which has integrally formed thereon a movable element or flange 82 which serves a similar function as the cylindrical member 18 of the prior embodiment. However, in this form, the adaptor is of one-piece unitary plastic construction, preferably polypropylene, including the element or flange, used for applying the torque to the adaptor and, hence, the blade/coupler, in the manner which will now be described. In this form, adaptor 81 includes a sleeve 84 having an axis 86 with flats 88 formed along opposite sides of the sleeve for receiving the blade/coupler flats similarly as in the previous embodiment. Sleeve 84 has an integrally projecting flange 90 at one end of sleeve 84.

Figure 7:
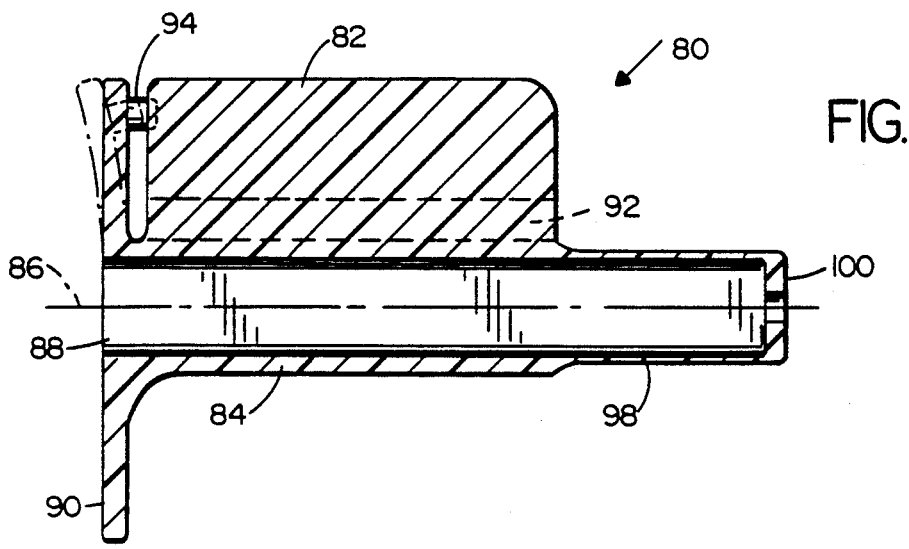
FIG. 7 is a longitudinal cross-sectional view of the adaptor thereof taken about on line 7—7 in FIG. 6.
Figure 8:
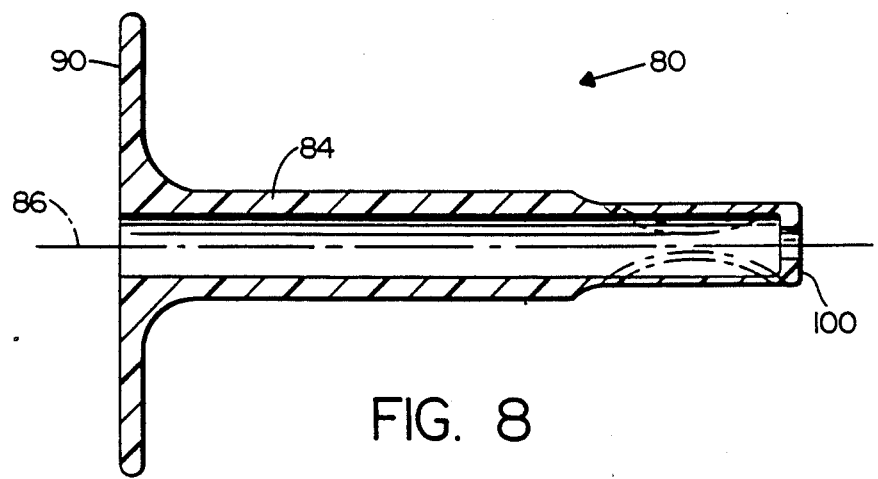
FIG. 8 is a longitudinal cross-sectional view thereof taken about on line 8—8 in FIG. 9.
Figure 9:
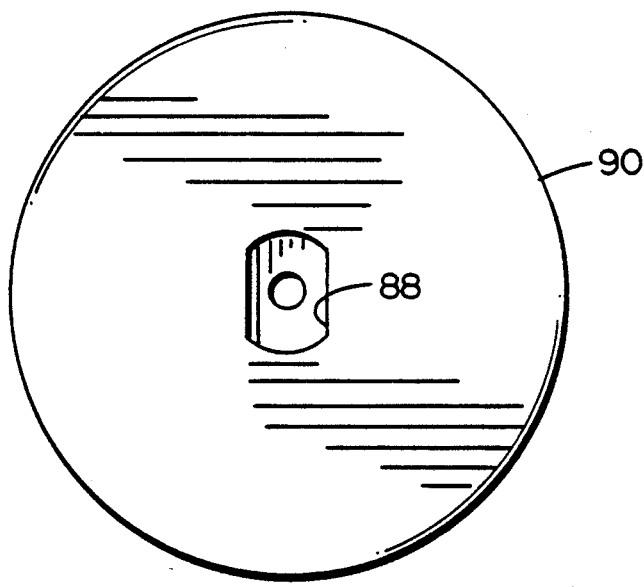
FIG. 9 is an end elevational view of the adaptor illustrated in FIG. 7 looking from left to right.
Figure 10:
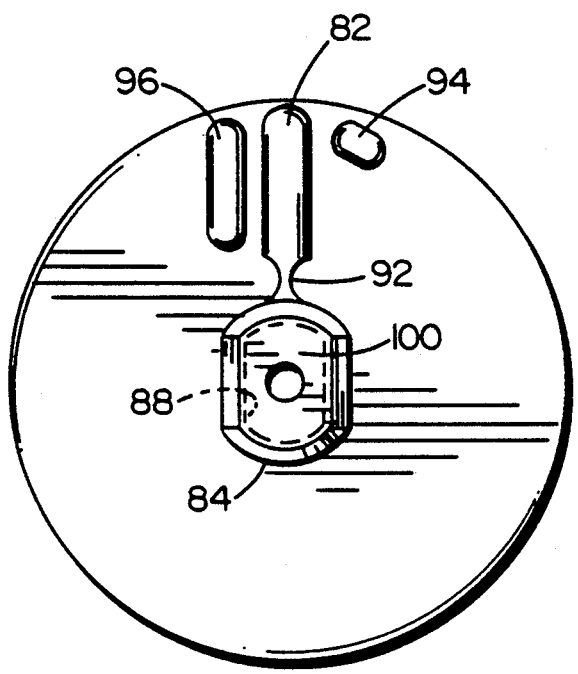
FIG. 10 is an end elevational view of the adaptor hereof taken from right to left in FIG. 7.

The element or flange 82 is integrally formed with the sleeve and extends substantially radially of the sleeve 84. However, the element or flange 82 is connected to sleeve 84 by a hinge 92 defined by an elongated weakened area or zone of element 82 directly adjacent sleeve 84. As best seen in FIG. 10, the hinge 92 is formed by reducing the material forming the thickness of the element or flange directly adjacent sleeve 84 whereby the element is movable about an axis coincident with hinge 92 and generally parallel to the axis 86 of sleeve 84. The element 82 is free for movement in opposite directions about hinge 92 and is spaced behind the flange 90 a predetermined distance as illustrated in FIG. 7.

On the back side of flange 90, there are provided a pair of circumferentially spaced projections 94 and 96. Projection 94 has a predetermined axial extent such that it extends into the path of movement of the forward edge of element 82 when element 82 is moved about hinge 92 in a direction tending to rotate the adaptor, hence the blade/coupler, in a tightening direction relative to the mount. Thus, by flexing element 82 about hinge 92 and engaging projection 94, adaptor 81 may be rotated to thread the blade/coupler onto the mount. As in the previous embodiment, the flange 90 is formed of material which is, to a degree, resilient. Thus, when the element 82 is deflected into engagement with projection 94 and a predetermined torque is applied, the flange 90 deflects under the applied loading imparted by element 82, causing the projection 94 to move forwardly out of the way of the leading edge of element 82. In this manner, element 82 may be displaced past projection 94, at which time the user will recognize that a predetermined magnitude of torque has been applied by the blade/coupler to the mount.

In order to rotate the blade/coupler in the opposite direction to unthread it from the mount, the blade/coupler is received with the sleeve 84 as before. The element 82 is then displaced about hinge axis 92 to engage projection 96. Projection 96 extends rearwardly a distance greater than projection 94 extends and, consequently, projection 96 may not be deflected from the path of movement of element 82. Therefore, virtually unlimited torque may be applied to the element 82 to rotate the adaptor and blade/coupler in a direction to unthread the blade/coupler from the mount.

Another feature of this embodiment of the invention resides in the thin-walled construction of the sleeve for that portion of the sleeve which projects rearwardly beyond the end of element 82. This thin-walled portion is indicated at 98. The wall 98 is thinned sufficiently such that it may be compressed by finger pressure. The thickened rear end portion 100 disposed beyond the compressible portion of the sleeve, however, is not laterally compressed. Thus, when finger pressure is applied to the flat sides of the thin-walled structure which, of course, are coincident with the plane of the flat blade of the blade/coupler, the compressed thin-walled portion provides an undercut or pinched-in zone to facilitate pulling the adaptor from the blade/coupler.

Consequently, it will be appreciated that the objects of the present invention are fully met in the above-described preferred embodiment of the invention. Particularly, blade/coupler 14 may be applied to the acoustical mount 30 without the danger of accidents resulting from the sharp edge of the blade and without over-tightening the connection, which would otherwise render disconnection of the blade/coupler 14 from mount 30 very difficult. That is, the tightening action is provided up to a predetermined torque and application of further torque results in a simple ratcheting or slipping action, without higher torque being applied to the threaded connection. Additionally, the same elements used to apply the blade/coupler 14 to mount 30 are used in the same manner to unthread blade/coupler 14 from mount 30. Unlimited torque, however, may be applied to the adaptor/member sub-assembly during unthreading, whereby any further tightening of the threaded connection through use of the device can be overcome. The delivery system is also provided in an inexpensive throw-away assembly whereby the assembly may be provided in a sterile environment and disposed of after use.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. Apparatus for attaching a surgical device to a mount wherein the surgical device includes a coupler carrying a surgical tool comprising:
   an adaptor including a sleeve for receiving the surgical tool and a flange adjacent one end of said sleeve;
   first means carried by said adaptor and engageable with the coupler when the surgical tool is received by the adaptor for rotating the coupler upon rotation of said adaptor;
   second means carried by said adaptor for rotating said adaptor to rotate the coupler including an element radially projecting from said sleeve behind said flange;
   third means cooperable between said second means and said adaptor flange and responsive to movement of said second means in one direction for limiting the torque applied by said adaptor to the coupler to a predetermined magnitude thereof when the surgical tool is being attached to the mount; and
   fourth means cooperable between said second means and said adaptor, and responsive to movement of said second means in the opposite direction, for applying a torque to the adaptor and coupler in said opposite direction in excess of said predetermined torque.

2. Apparatus according to claim 1 wherein said sleeve has a bore and said first means comprises a pair of flats carried thereby with said bore for engaging flats on the coupler.

3. Apparatus according to claim 1 in combination with said surgical device, said adaptor having a generally conical surface configured to guide said surgical tool into said sleeve.

4. Apparatus according to claim 1 wherein said third means comprises and a projection carried by said flange for engagement by said element upon movement thereof in said one direction to rotate said adaptor and the coupler.

5. Apparatus according to claim 4 wherein said element is pivotally carried by said sleeve.

6. Apparatus according to claim 5 wherein said adaptor is formed integrally of plastic material, said element being flexible about its pivot axis to engage said projection, said flange being flexible in an axial direction to enable disengagement of the element and the projection in response to attaining the predetermined magnitude of torque.

7. Apparatus according to claim 5 wherein said adaptor is formed integrally of plastic material, said element being pivotally carried by said sleeve for pivotal movement about an axis generally parallel to and radially spaced from the axis of said sleeve, said flange being flexible in an axial direction to enable disengagement of the element and the projection in response to attaining the predetermined magnitude of torque.

8. Apparatus according to claim 1 wherein said sleeve has a portion adjacent the end thereof opposite side sleeve which is compressible by finger pressure to facilitate removal of the adaptor and coupler one from the other.

9. Apparatus according to claim 8 wherein said sleeve portion is of reduced wall thickness relative to other portions of said sleeve, said opposite end of said sleeve having a non-compressible portion to provide manual purchase of said sleeve by grasping and compressing said thin-walled portion in advance of said non-compressible portion.

10. Apparatus for attaching a surgical device to a mount wherein the surgical device includes a coupler carrying a surgical tool comprising:
    an adaptor including an elongated sleeve, having an axis, for receiving the surgical tool, a flange having an abutment, guide surfaces engageable with the coupler when the surgical tool is received by the adaptor for rotating the coupler upon the rotation of said adaptor;
    a generally radially extending element carried by said adaptor for rotating the adaptor to rotate the coupler, said element being movable in opposite directions about an axis non-coincident with the axis of said sleeve, said element being cooperable with said abutment in response to rotation of said element about its axis in one direction to rotate the adaptor and coupler about the axis of said sleeve and to limit the torque applied by said adaptor to the coupler to a predetermined magnitude thereof; and
    a second abutment carried by said flange, said element being cooperable with said second abutment in response to rotation of said element about its axis in the opposite direction for applying a torque to the adaptor and coupler in excess of said predetermined magnitude of torque.

11. Apparatus according to claim 10 wherein said adaptor is formed integrally of plastic material with said element being secured to said sleeve by a weakened portion of plastic material and of a thickness reduced from the thickness of said element.

12. Apparatus according to claim 10 wherein said sleeve has an end portion remote from said flange of reduced wall thickness, enabling compression thereof by finger pressure to facilitate removal of the adaptor from the blade/coupler.

13. A method for attaching a surgical device to a mount wherein the surgical device includes a coupler carrying the surgical tool, comprising the steps of:
    providing an adaptor having a sleeve containing the surgical tool and engageable with the coupler such that the coupler and adaptor may be rotated in one direction upon rotation of said adaptor in said one direction;
    providing a first member carried by the adaptor and movable in opposite directions;
    providing a second non-movable member carried by a flange on the adaptor and engageable by said first member;
    moving said first member in one direction to engage said second member to rotate the adaptor and coupler in one rotary direction;
    limiting the torque applied by said adaptor to the coupler to a predetermined magnitude thereof in response to movement of said member is said one direction by enabling deflection of said flange carrying said second member thereby displacing said flange and said second member away from said first member upon reaching the predetermined torque such that the first member, moving in said one direction, moves past the second member;
    providing a third substantially non-movable member spaced from said second member and carried by said flange, said third member being dimensioned to engage said first ember and substantially preclude movement of said first ember past said third member in response to movement of said first member in the opposite direction;

moving said first member in the opposite direction to engage said third member to rotate the adaptor and coupler in the opposite rotary direction; and applying a torque to said first member when moving it in said opposite direction and against said third member to rotate said adaptor and coupler in said opposite rotary direction, in excess of said predetermined magnitude of torque, thereby to detach the surgical device and the mount.

* * * * *